(12) United States Patent
Mosseri

(10) Patent No.: US 6,261,265 B1
(45) Date of Patent: Jul. 17, 2001

(54) DEVICE FOR PROTECTING A CUTTING AND/OR DRILLING TOOL

(76) Inventor: Raphael Mosseri, 38, Rue Beaujon, 75008 Paris (FR)

( * ) Notice: Subject to any disclaimer, the term of this patent is extended or adjusted under 35 U.S.C. 154(b) by 0 days.

(21) Appl. No.: 09/486,337

(22) PCT Filed: Aug. 24, 1998

(86) PCT No.: PCT/FR98/01838

§ 371 Date: Mar. 28, 2000

§ 102(e) Date: Mar. 28, 2000

(87) PCT Pub. No.: WO99/09898

PCT Pub. Date: Mar. 4, 1999

(30) Foreign Application Priority Data

Aug. 25, 1997 (FR) .................................................. 97 10627

(51) Int. Cl.[7] .................................................. A61M 5/32
(52) U.S. Cl. .......................................... 604/198; 606/167
(58) Field of Search ........................ 604/161.01, 164.08, 604/164.12, 166.01, 192, 198, 263; 606/167, 170, 172, 181

(56) References Cited

U.S. PATENT DOCUMENTS

| 4,725,267 | 2/1988 | Vaillancourt . | |
|---|---|---|---|
| 4,850,996 | 7/1989 | Cree . | |
| 4,985,021 | 1/1991 | Straw et al. . | |
| 5,049,136 | 9/1991 | Johnson . | |
| 5,250,064 | 10/1993 | Schneider | 606/167 |
| 5,330,492 | 7/1994 | Haugen | 606/167 |
| 5,360,408 | 11/1994 | Vaillancourt . | |
| 5,364,370 | 11/1994 | Szerlip et al. . | |
| 5,423,766 | 6/1995 | Di Cesare | 604/192 |

FOREIGN PATENT DOCUMENTS

| 0 583 992 | 2/1994 | (EP) . |
| 2 700 960 | 8/1994 | (FR) . |
| WO 90/11725 | 10/1990 | (WO) . |
| WO 94/01152 | 1/1994 | (WO) . |

*Primary Examiner*—Anhtuan T. Nguyen
(74) *Attorney, Agent, or Firm*—Young & Thompson

(57) ABSTRACT

The invention concerns a device for protecting a cutting and/or drilling tool (A), comprising: means (4) for isolating from outside a cutting and/or drilling distal part (12) of the tool, said means being connected to a non-cutting and/or non-drilling part of the tool with limited relative mobility and having an opening for said distal part to move between a protected position, wherein the means for isolating the tool encloses at least partially said distal part, and a working position, wherein said distal part is released from the means isolating the tool; elastic means (13) for returning the distal part in the protected position, said distal part being capable of moving towards its working position by the effect of an external pressure (F) countering the elastic return force.

18 Claims, 4 Drawing Sheets

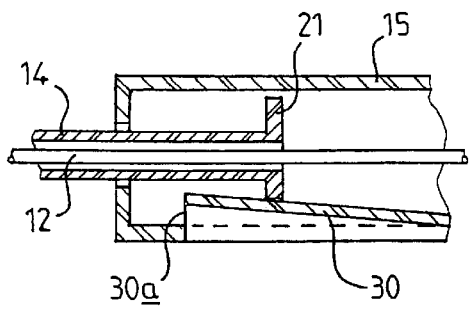
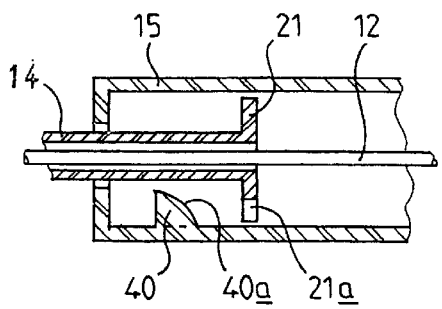
FIG.11  FIG.12
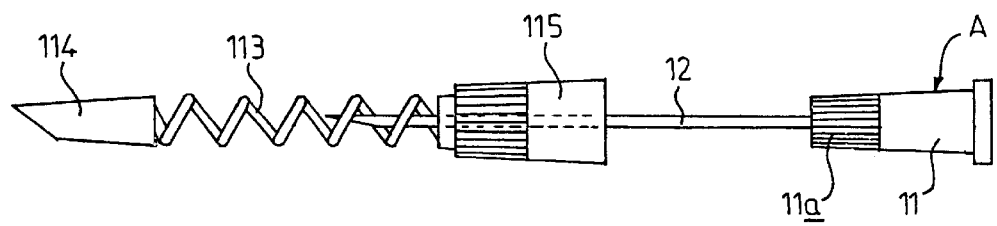
FIG.13
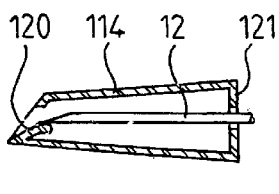 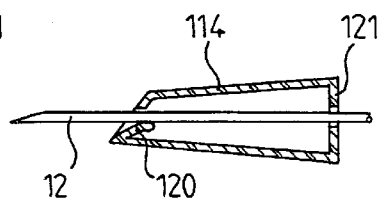 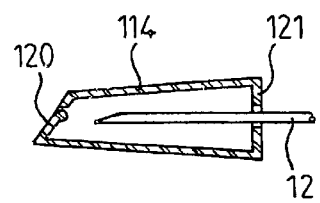
FIG.14A  FIG.14B  FIG.14C
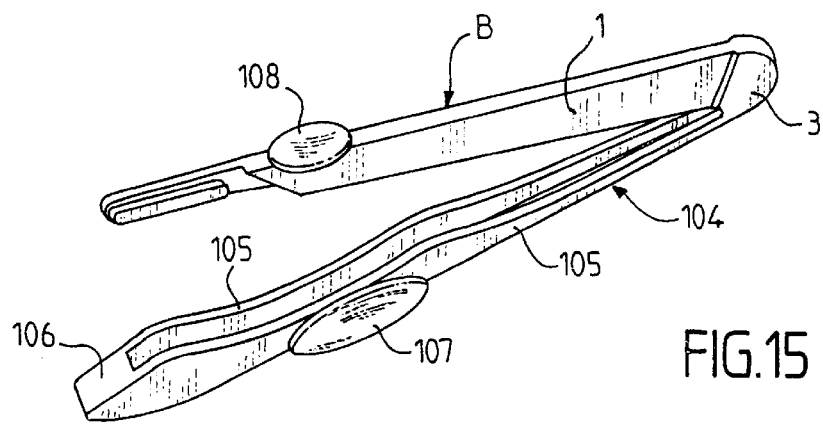
FIG.15

DEVICE FOR PROTECTING A CUTTING AND/OR DRILLING TOOL

The present invention relates to a protective device for a cutting and/or perforating tool, particularly for a medical instrument such as a scalpel or the needle of a syringe.

In the medical field, numerous cutting and/or perforating instruments are used by care givers, infirmaries, doctors, surgeons and related personnel, who can injure themselves in the course of handling.

There can be distinguished on the one hand the risks and on the other hand the consequences.

The present risks encountered during use:

a) of a cutting instrument, such as a scalpel (outside the operating room), can give rise to
   either accidental wounding of the operator, either by himself or by a third party during handling over the instrument,
   or a wounding of a helper upon return of the instrument,
   or the sterilization of the operating table when the scalpel is deposited on the instrument table;

b) of a perforating instrument, such as a syringe needle, can give rise to accidental pricking of the care giver
   either by a needle already sterilized after opening the package,
   or by a needle already having been used with the risk of inoculation of a blood product (by an instrument either already laid on the table or in the course of handling).

The consequences are:

a) generally speaking, both for a scalpel and for a needle, a risk of transmission of infectious, viral (hepatitis virus, HIV virus, . . . ), bacterial or parasitic agent. Certain harm can be irreversible;

b) from an anatomic and functional standpoint (more particularly with scalpels), cutting tendons, cutting nerves or collateral peduncle of a finger; the prognosis is sometimes very grave as to these cuts, giving rise to functional incapacity which can be permanent with consequences on a professional level but also on the operative level for normal life.

Any accident gives rise to carrying out a protocol which can extend for several years and the indemnification of this accident can hit the public health budget particularly hard.

The problem connected to the protection of personnel using cutting and/or perforating tools is particularly sensitive in the medical field because it can have dramatic consequences for human health.

However, despite the gravity of this problem and the existence of very infectious diseases for a number of years, no reliable and efficacious solution has yet been found to overcome these drawbacks.

The present invention therefore has for its object to eliminate the mentioned drawbacks, to satisfy the requirements of public health and to provide a device for general protection for a cutting and/or perforating tool, and more particularly for a medical instrument.

To this end, the invention has for its object a protective device for a cutting and/or perforating tool, characterized in that it comprises:

means to isolate from the outside a distal cutting and/or perforating portion of the tool, this means being connected to a proximal non-cutting and/or non-perforating portion of the tool with limited relative movement and having an opening for the passage of said distal portion between a protective position, in which the means to isolate the tool surrounds at least partially said distal portion, and a working position, in which said distal portion is disengaged from the means to isolate the tool, and resilient means to return the distal portion to the protective position, said distal portion being adapted to move toward the working position under the influence of external pressure opposing the force of the resilient return means.

In the first embodiment, the invention comprises the following additional characteristics:

the device is adapted to protect a scalpel or the like, and comprises:
   means to isolate from the outside a blade forming the distal portion of the scalpel, this means being connected to a sleeve forming a proximal portion of the scalpel with limited relative movement and having an opening for the passage of said blade between a protective position, in which said means at least partially surround said blade, and a working position, in which said blade is disengaged from said means, and
   resilient means to return the blade to the protective position, said blade being adapted to move toward the working position under the influence of external pressure opposing the force of the resilient return means, said isolation means having the general shape of a fork whose tines of the fork define the mentioned opening for the passage of the blade of the scalpel, said means being connected to the handle of the scalpel so as to permit displacement of the fork in the plane of the blade, said fork being connected to the proximal end of the handle of the scalpel by a connection region serving as a hinge, to permit moving toward each other of the handle and the fork when the user has gripped them with the fingers in the manner of the tines of a dissecting tweezers, to bring the blade to its working position;
   each tine of the fork extends in a plane substantially parallel to the plane of the blade and has a contour which at least circumscribes the contour of the blade in its protective position;
   the handle of the scalpel and the fork are functionally connected to each other by a region of material having its own elasticity to permit relative moving apart and together of the handle and the fork by resilient deformation of this region, the latter serving also as the resilient return means;
   the handle of the scalpel and said fork are made in a single piece and of the same material;
   the handle of the scalpel and the fork are articulated to each other and the resilient return means is constituted by a spring interposed between them;
   said fork comprises abutments to prevent the displacement of the blade beyond the protective and working positions;
   the fork comprises a handle serving as an end of path abutment for the handle of the scalpel when the blade is displaced into its working position;
   the handle of the fork has a transverse cross-section of general U shape defining a recess for receiving the handle of the scalpel when it is brought to its working position;
   the tines of the fork are connected by a bridge of material serving as an end of path abutment for the handle of the scalpel when the blade is returned to its protective position;

the fork has on its two external side surfaces a convex shape to serve as a gripping surface for the fingers of the user.

In a second embodiment, the invention comprises the following additional characteristics:

the device is adapted to protect a needle, and comprises:
means to isolate from the outside a point forming the distal perforating portion of the needle, this means being connected to a ferrule for connection to a syringe forming the proximal portion of the needle with limited relative movement and having an opening for the passage of said point between a protective position, in which said means at least partially surrounds said point, and a working position, in which said point is disengaged from said means, resilient means to return the point to the protective position, said point being adapted to move toward the working position under the influence of external pressure opposing the force of the resilient return means, said isolation means being constituted by a transparent tube open at its two ends, through which is slidably mounted the distal portion of the needle, and anti-return blocking means to block the point of the needle in a protective position, said blocking means being adapted to engage on the tube by relative movement between said tube and needle under the influence of an external force to prevent the movement of the point toward its working position;

the blocking means is connected to the ferrule of the needle and a proximal portion of the tube and is adapted to free this blocking means during sliding of the tube relative to the point in a direction opposite to the movement toward its working position, to obtain resilient engagement of the blocking means against said proximal portion of the tube;

the resilient means is a coil spring mounted axially about the needle and connecting the ferrule of the needle to a proximal portion of the tube and in that the spring is engaged in a supplemental protective envelope fixed to the ferrule of the needle and slidably surrounding the mentioned tube;

the blocking means is secured to the envelope and is adapted to coact with a proximal collar of the tube;

the resilient means is a coil spring which is molded at one end to the mentioned tube, and at its other opposite end, to a handle in which can be received the connecting ferrule of the needle;

the blocking means is connected to the tube and adapted to engage resiliently on the distal end of the tube to close the passage for the point toward its working position, during sliding of the tube relative to the point in a direction opposite to the movement toward its working position;

said tube having at its distal end a lower flat annular anti-sliding surface, constituted for example by roughenings and wedges and/or coated with adhesive material, said annular surface serving also for viewing and targeting the vessel or the body space for the needle;

the tube has longitudinal marking, for example a projecting rib or a colored line, arranged laterally so as not to mask the visibility of the needle and the periphery of the vessel or body space to be reached, so as to mark the general direction of the edges of the vessel or of the body space.

The invention will be better understood, and other objects, details, advantages and characteristics of it will become more clearly apparent in the course of the following detailed description of several particular embodiments of the invention that are presently preferred, given solely by way of illustration and not limiting, with reference to the accompanying schematic drawings, in which:

FIGS. 11 and 12 are fragmentary axial cross-sectional views of two other modifications of a protective device for a needle;

FIG. 13 is an exploded view of another embodiment of the protective device for a needle;

FIGS. 14A to 14C are fragmentary axial cross-sectional views of the device of FIG. 13, respectively in a protective position before use, in a working position, and in a blocked condition in the protective position; and FIG. 15 is a perspective view of a modified embodiment of a protective device for a scalpel.

Figure 1:
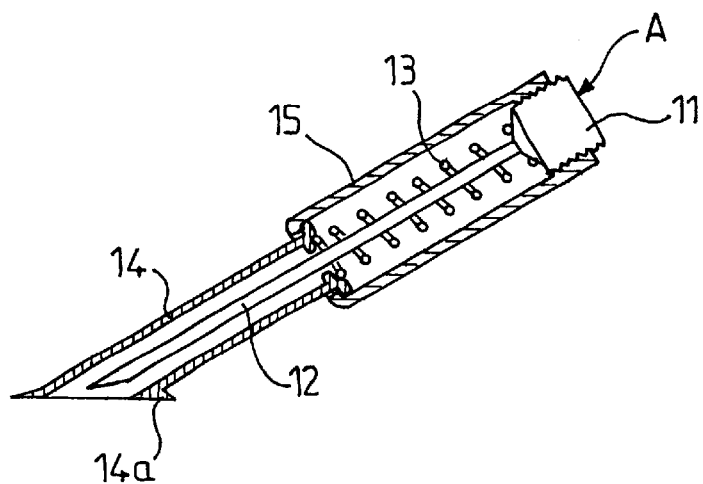
FIG. 1 is a schematic view in axial cross-section of a protective device for a needle, according to the invention.

According to the particular example of embodiment shown in FIGS. 3 to 7, a first embodiment of the protective device according to the invention is suitable for a scalpel B. This scalpel B, which is known per se, comprises a handle 1 carrying at its distal portion a blade 2. The handle 1 is connected at its proximal end by a connecting zone 3 to a fork-shaped element 4 serving to isolate the blade from the outside. The fork-shaped element 4 comprises two tines 5 substantially parallel and spaced from each other, which are interconnected by a handle 6 forming the proximal portion of the fork-shaped element 4. The handle 1 of the scalpel and the fork-shaped element 4 can be made of a single piece and of the same material, such as plastic. Thus, the connecting region 3 serves as a "hinge" between the handle 1 of the scalpel and the fork-shaped element 4 to permit relative movement together and apart of these latter in the manner of a dissecting tweezers. The self-elasticity of the material at the level of the connecting zone 3 automatically ensures the resilient return of the fork-shaped element 4 toward the handle 1 of the scalpel B.

As a modification, there could also be provided an articulation between the handle 6 of the fork 4 and the handle 1 of the scalpel B, with a helicoidal return spring mounted on the articulation axle or a blade spring interposed between the two handles. In this case, the handle 1 of the scalpel B and the fork-shaped element 4 could be disassemable and separately made.

Figure 5:
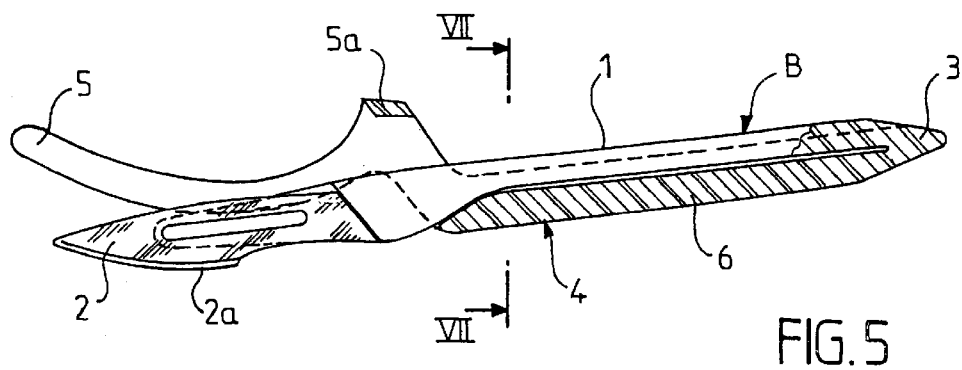
FIG. 5 is a view analogous to that of FIG. 4, but showing the blade of the scalpel in its working position.
Figure 6:
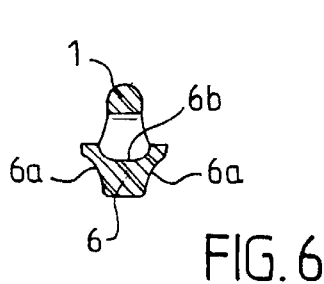
FIGS. 6 and 7 are views in transverse cross-section respectively on the lines VI—VI of FIG. 4 and VII—VII of FIG. 5.
Figure 7:
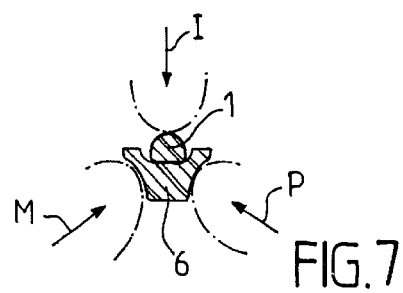

As is visible in FIGS. 6 and 7, the handle 6 of the fork 4 has a transverse cross-section of generally U-shaped to receive the handle 1 of the scalpel B when the device is brought to its working position, as shown in FIG. 5. The handle 6 of the fork 4 has on its two external side surfaces 6a a concave shape to serve as a gripping surface for the thumb P and the middle finger M of the hand of the user, the index finger I bearing on the upper portion of the handle 1 of the scalpel B, when the user grips the device in the manner of a pen.

It will be noted that this device can equally well be used by a right-handed person as by a left-handed person.

Figure 4:
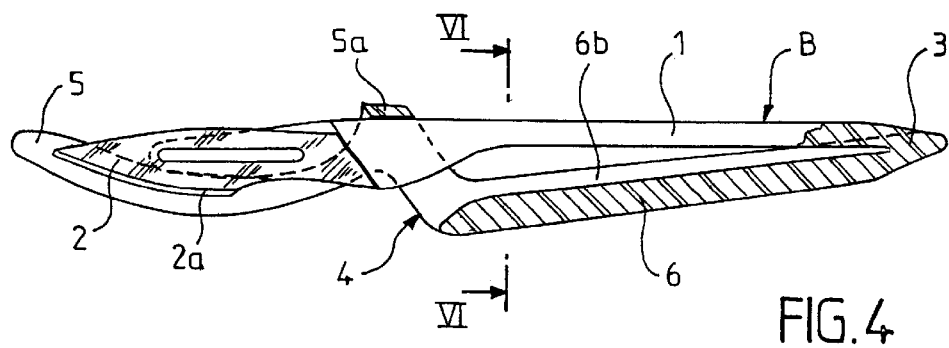
FIG. 4 is a longitudinal cross-sectional view on the line IV—IV of FIG. 3, the blade of the scalpel being in its protective position.

As is better seen in FIGS. 4 and 5, each tine 5 of the fork extends in a plane substantially parallel to the plane of the blade 2 of the scalpel and on opposite sides of the latter. When the blade 2 is in its protective position shown in FIG. 4, it will be seen that the tines 5 have, in a projection perpendicular to the plane of the blade, an external contour which completely envelopes the edge 2a of the blade. The two tines 5 of the fork are also connected by a bridge 5a of material which surmounts the handle 1 of the scalpel B to prevent relative supplemental spacing of the handles 1 and 6 from the protective position shown in FIG. 4. Otherwise, it would be possible to space upwardly the handle 1 relative to the handle 6 and to introduce for example a finger between the blade 2 and the tines 5 of the fork, which finger could thus be sliced under the force of the resilient return of the connection zone 3.

The operation of the device shown in FIGS. 3 to 7 will now be briefly described.

In its rest position, the device is as shown in FIG. 4, which is to say that the blade 2 of the scalpel B which is laterally surrounded by the tines 5 of the fork, said tines 5 covering both in length and in height the cutting edge 2a of the blade 2. Thus, the blade 2 is isolated from the exterior in its protective rest position. There could also be provided an unlockable locking means to lock the device in this position.

When it is desired to disengage the blade 2 of the device, it suffices to place the fingers on the handles 1 and 6 and to grip the fingers, which has the effect of bringing together the handles against each other until the handle 1 comes into abutment in the recess 6b of the handle 6. In the position shown in FIG. 5, the tines 5 of the fork 4 move relative to the blade 2, thereby uncovering the useful portion of the blade. If the device escapes through mishap from the hand of the user, the blade will automatically be returned to the protective position under the influence of the resilient return force of the connection zone 3.

In FIG. 15, there is shown a modified embodiment of a protective device for a scalpel B which differs from the device of FIGS. 3 to 7 only by the following characteristics:

- the fork-shaped element 104 comprises two substantially parallel tines 105 spaced from each other and connected at one end by the connection zone 3 and at their other free end by a bridge 106 of material which is adapted to serve as an upper abutment for the blade (not shown in FIG. 15) of the scalpel, to prevent supplemental relative spacing of the handle 1 relative to the fork-shaped element 104, the two tines 105 also being connected substantially at their middle by a cross-piece (not shown in FIG. 15), which serves as a lower abutment for the handle 1,
- a concave impression 107 is formed laterally on each tine 105 of the fork element 104 to serve as a gripping surface for the fingers, in the manner of the surfaces 6a of the embodiment of FIG. 6, in a concave impression 108 provided on the upper side of the handle 1 to serve as a gripping surface for the index finger of the hand of the user.

The operation of the modified embodiment shown in FIG. 15 is substantially analogous to that of the embodiment shown in FIGS. 3 to 7.

Another embodiment of the device of the invention will now be described with reference to FIGS. 1 and 2.

The perforating tool used in this case a needle A for a syringe S, this needle comprising at its proximal portion an enlarged tubular cylindrical ferrule 11 prolonged by a surrounded tubular distal portion 12 of smaller diameter. This perforating distal portion 12 is disposed slidably axially in a transparent protective tube 14 which is connected at its proximal end by a coil spring 13 to the ferrule 11 of the needle. Preferably, this tube 14 is of semi-rigid material. The distal end 14a of the tube 14 is preferably bevelled to permit perforation of the skin P of a user in an inclined direction as is conventionally the case. This distal end 14a is also reinforced to resist the pressure of the tube 14 against the skin P during penetration of the point of the needle 12.

To avoid any trial and error, it is also important that the needle be positioned precisely and correctly when the skin is to be pricked to access a vessel or a body space.

To this end, there can be provided at the distal end 14a of the tube 14, a lower flat angular anti-skid surface, constituted for example by roughening or wedges and/or covered with an adhesive material. Thus, during pressing the tube against the skin, the tube will not risk slipping and destroying the precision of the injection.

Moreover, this distal annular surface facilitates viewing and targeting the vessel or the body space by the needle. Thus, before even penetrating the skin, the operator can adjust his aim by successive manipulations of the device.

As a modification, there could also be provided a marking along the tube, for example a projecting rib or a colored line, arranged laterally so as not to mask the visibility of the needle and the periphery of the vessel or the body space to be reached, so as to enclose the general direction of the edges of the vessel or of the body space.

The inclination of the surface is preferably 45° relative to the axis of the needle for vascular extractions or perpendicular to the latter to reach a rachidian space for example.

Finally, it will be noted that the device of the invention is an automatically integrated safety device and permits, namely as soon as the needle leaves its packaging, before, during and after manipulation. This safety device need not be activated by the operator.

There can also be provided an external protective envelope 15 connected at its proximal end to the ferrule 11 of the needle A and mounted slidably about the tube 14 at its distal end. This envelope 15 permits isolating from the outside the spring 13 and can also serve for guiding the tube 14 in the course of its movement.

Figure 2:
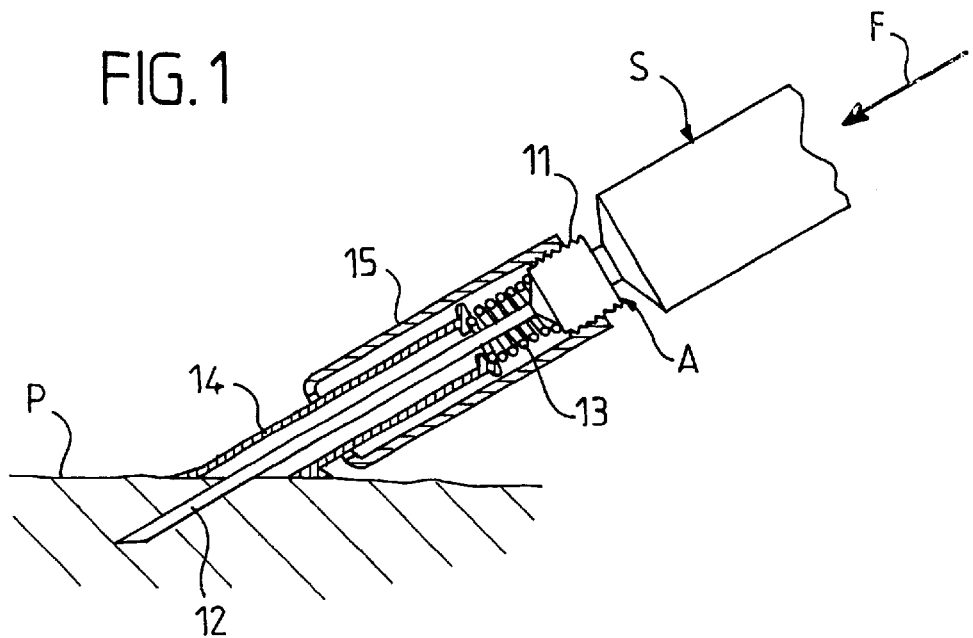
FIG. 2 is a view similar to FIG. 1, but showing the needle in its working position.
Figure 3:
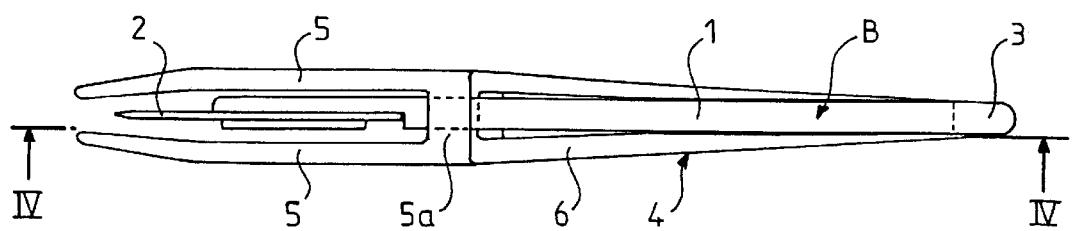
FIG. 3 is a top plan view of a protective device for a scalpel, according to the invention.

The operation of the device shown in FIGS. 1 and 2 will now be briefly explained.

In the rest position shown in FIG. 1, the perforating portion or point 12 of the needle 1 is completely retracted within the tube 14, which tube 14 has a length less than that of the distal portion 12.

When a user has applied the distal end 14a of the tube 14 against the skin P of a patient, as shown in FIG. 2, he exerts a pressure in the axial direction F of the device at the level of the ferrule 11 of the needle A, for example by means of a syringe S, which has the effect of compressing the spring 13 and to cause the perforating portion 12 of the needle to slide in the tube 14 until said perforating portion emerges from the tube and penetrates the skin P. It will be understood that as soon as pressure is released, at the level of the syringe, the needle 12 will be returned to its protective position by the return spring 13.

Figure 8:
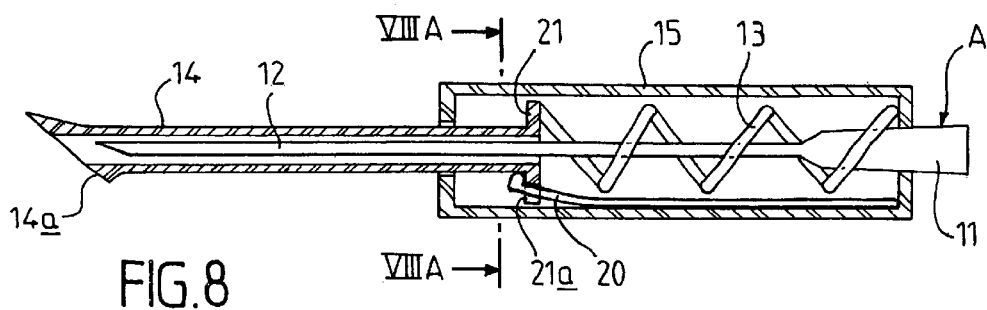
FIG. 8 is a view analogous to FIG. 1, but showing a modified embodiment of the invention for protection of a needle.
Figure 9:
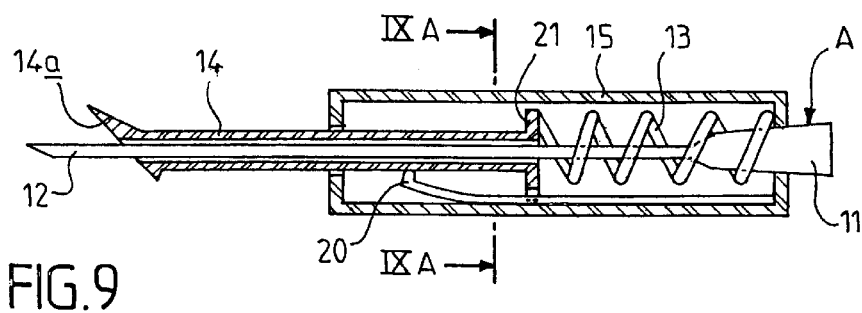
FIGS. 9 and 10 are views analogous to FIG. 8, but showing respectively the needle in its working position and in its position blocked in the protective position.
Figure 10:
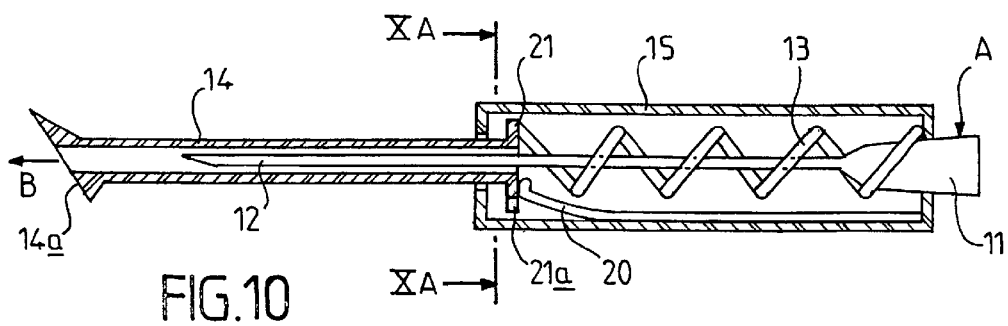

In FIGS. 8 to 10, there is shown a modified embodiment in which the envelope 15 is provided on its internal sidewall with a resiliently deformable blocking tongue 20. This blocking tongue 20 is fixed to an end of the internal wall of the envelope 15 and has at its opposite free end an incurved portion adapted to coact with the collar 21 formed at the proximal end of the tube 14. This collar 21, which extends radially outwardly, slides within the envelope 15 and comprises at its periphery a reinforcement 21a for the passage of the free end of the blocking tongue 20.

Figure 8A:
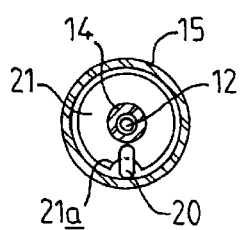
FIGS. 8A, 9A and 10A are transverse cross-sectional views in the direction of the arrows VIII-A, IX-A, and X-A of FIGS. 8–10, respectively.

The operation of the device shown in FIGS. 8 to 10 will now be described. In the position shown in FIGS. 8 and 8A, the tube 14 is urged toward its protective position for the point 12 of the needle, by the spring 13, the collar 21 of the tube 14 coming into abutment against the inturned end of the blocking tongue 20 which passes through the reinforcement 21a of the collar 21.

Figure 9A:
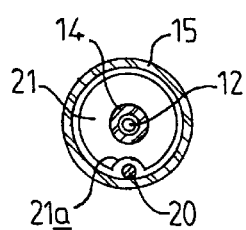

The tube 14 is brought to its working position shown in FIGS. 9 and 9A, by pressing the enlarged distal portion 14a against the skin of the user, to uncover the point 12 of the needle. The collar 21 of the tube 14 against which the spring 13 bears will compress this latter and slide within the envelope 15. The collar 21 slides along the blocking tongue 20 in the direction of its free end.

When the operation is completed, the tube 14 returns to its position shown in FIG. 8, under the return force of the spring 13.

Figure 10A:
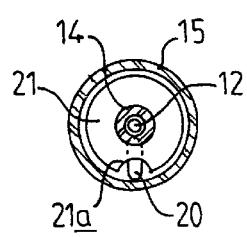

Then, to render the device non-reusable, the operator exerts a tractive force on the tube 14, in the direction of the arrow B in FIG. 10, until the collar 21 passes the free inturned end of the blocking tongue 20, said tongue 20 flexes slightly outwardly, and then returns resiliently inwardly to abut against the collar 21, above the reinforcement 21a, thereby preventing any return movement of the tube 14 to uncover the point 12, as is seen in FIG. 10A.

Although not shown, the blocking tongue 20 could be replaced by a non-return blocking means adapted to coact with the collar 21, by relative rotation of the tube 14, relative to the envelope 15, a snap means being provided between the periphery of the collar 21 and the internal wall of the envelope 15.

In the modification of FIG. 11, the blocking tongue 20 is replaced by an inclined ramp 30 which is molded with the envelope 15, the ramp 30 extending inwardly of the envelope 15 from its proximal position toward its distal position. The collar 21 is adapted to slide by its reinforcement 21a on the ramp 30 which has a complementary profile. The ramp 30 is open at its distal portion, for reasons of demolding. This ramp 30 is resiliently deformable, during its passage over the collar 20, to bring the tube 14 into the blocked protected position.

In another modification shown in FIG. 12, the ramp 30 is replaced by a tooth 40 which has an incurved profile 40a turned toward the reinforcement 21a of the collar 20, to permit its release, and an opposite surface parallel to the plane of the collar 21 to serve as a non-return bearing surface, in the protected blocking position of the tube 14. This tooth 40 is also resiliently deformable when the collar 21 passes over it.

There could also be provided, without departing from the scope of the invention, a resiliently deformable collar 21 instead of the ramp 30 or the tooth 40.

In another embodiment shown in FIG. 13, the device of the invention comprises a tube 114 whose proximal portion is connected to a spring 113 which is in turn connected by its proximal end winding with a handle 115. The elements 113 to 115 are of one-piece construction made by molding.

The ferrule 11 of the arrow A is adapted to be received in the handle 115, the ferrule 11 comprising on its peripheral wall channels 11a which are adapted to engage in corresponding channels formed on the internal wall of the handle 115, with a locked adjustment for their connection.

As is seen in FIGS. 14A to 14C, the tube 114 comprises at the level of its distal portion a tongue 120 which is resiliently deflected toward the interior of the tube 114 and maintained in this position by the point 12 of the needle. At its proximal portion, the tube 114 comprises a collar 121 radially projecting inwardly, through which passes the point 12 of the needle A for its guidance.

In the position shown in FIG. 14A, the point 12 of the needle A is protected by the tube 114 and retains the blocking tongue 120 in an inactive position. When the point 12 of the needle is brought to its working position, the point 12 slides over the blocking tongue 120 which is still held in an inactive position.

After use, to render the device non-reusable, the user exerts a traction on the tube 114, to space the point 12 of the needle from the tongue 120 which is elastically returned into a position in which it closes the passage of the tube 114, at its distal end, thereby preventing the exit of the point 12 from the tube 114.

Here it will be seen by those skilled in the art that the invention is not limited to a scalpel or a needle, but can be applied to any cutting and/or perforating element, in fields other than medicine. It is also clear that the invention is not limited either to the form or to the structure of the illustrated devices, any other form or structure permitting performing the same functions forming a part of the scope of the present invention.

Although the invention has been described in connection with two particular embodiments, it is evident that it is not thereby limited and that it comprises all the technical equivalents of the described means as well as their combinations if the latter enter into the scope of the invention.

What is claimed is:

1. Protective device for a cutting tool (B), comprising:

a scalpel (B) constituting said cutting tool means (4, 104) to isolate from the exterior a blade (2) forming the distal portion of the scalpel, this means being connected to a handle (1) forming the proximal portion of the scalpel with limited relative mobility and having an opening for the passage of said blade between a protected position, in which said means at least partially surrounds said blade, and a working position, in which said blade clears said means, and resilient means (3) to return the blade to its protected position, said blade being adapted to move toward its working position under the force of an external pressure (M, I, P) opposing the resilient return force, said isolation means having the general shape of a fork (4, 104) of which the tines (5, 105) of the fork define the mentioned opening for the passage of the blade of the scalpel, said means being connected to the handle (1) of the scalpel so as to permit movement of the fork in the plane of the blade, characterized by the fact that said fork (4, 104) is connected to the proximal end of the handle (1) of the scalpel by a connecting zone (3) serving as a hinge, to permit relative movement of the handle (1) and the fork (4, 104) toward each other when the user grips them with the fingers in the manner of the blades of a dissecting tweezers, to bring the blade to its working position.

2. Device according to claim 1, characterized in that each tine (5, 105) of the fork extends in a plane substantially parallel to the plane of the blade and has a contour which at least circumscribes the contour of the blade in the protected position.

3. Device according to claim 1, characterized in that the handle (1) of the scalpel and the fork (4, 104) are operatively interconnected to each other by a zone of material (3) having self-elasticity to permit relative movement toward and away from each other of the handle and the fork by resilient deformation of this zone, the latter serving also as resilient return means.

4. Device according to claim 3, characterized in that the handle (1) of the scalpel and said fork (4, 104) are made of a single piece and of a same material.

5. Device according to claim 1, characterized in that the handle (1) of the scalpel and the fork (4, 104) are articulatedly interconnected and the resilient return mens is constituted by a spring interposed between them.

6. Device according to claim 1, characterized in that said fork (4, 104) comprises abutments to prevent the displacement of the blade beyond the protected and working position.

7. Device according to claim 6, characterized in that the fork (4) comprises a handle (6) serving as an end of path abutment for the handle of the scalpel when the blade is displaced into its working position.

8. Device according to claim 7, characterized in that the handle (6) of the work (4) has a transverse cross-section of general U shape defining a recess (6b) to receive the handle (1) of the scalpel when it is brought to its working position.

9. Device according to claim 6, characterized in that the tines (5, 105) of the fork are connected by a bridge in material (5a, 106) serving as an end of path abutment for the handle of the scalpel when the blade is returned to its protected position.

10. Device according to claim 1, characterized in that the fork (4, 104) has on its two external side surfaces a concave shape (6a, 107) to serve as a gripping surface for the fingers (P, M) of the user.

11. Integrated protective device for a perforating tool (A), comprising:

a needle (A) constituting said perforating tool, means (14, 114) to isolate from the outside a point (12) forming the distal perforating portion of the needle, this means being connected to a ferrule (11) for connection to a syringe (S) forming the proximal portion of the needle with limited relative mobility and having an opening for the passage of said point between a protective position, in which said means at least partially surrounds said point, and a working position, in which said point clears said means, resilient means (13, 113) to return the point to its protected position, said point being adapted to move toward its working position under the influence of an external pressure (F) opposing the resilient return force, said isolation means being constituted by a transparent tube (14, 114) open at its two ends, through which is slidably mounted the distal portion (12) of the needle, characterized by the fact that it comprises anti-return blocking means (20, 30, 40, 120) to block the point of the needle in a blocked protected position, said blocking means being maintained in its inactive position by the needle or the tube against which it bears in the protected position, said blockage means being adapted to engage the tube resiliently, from the protected position, by relative sliding between the tube and the point (12) of the needle in a direction opposite to the movement toward its working position, under the action of an external force, to the blocked protected position, to prevent the displacement of the point toward its working position.

12. Device according to claim 11, characterized in that the blocking means (20, 30, 40) is connected to the ferrule (11) of the needle and a proximal portion (21) of the tube (14) is adapted to clear this blocking means during sliding of the tube toward its blocked protected position, to obtain resilient engagement of the blocking means against said proximal portion of the tube.

13. Device according to claim 11, characterized in that the resilient means is a coil spring (13) mounted axially about the needle and connecting the ferrule (11) of the needle to a proximal portion (21) of the tube (14) and in that the spring is disposed in a supplemental protective envelope (15) affixed to the ferrule (11) of the needle and slidably surrounding the mentioned tube (14).

14. Device according to claim 13, characterized in that the blocking means (20, 30, 40) is secured to the envelope (15) and adapted to coact with a proximal collar (21) of the tube (14).

15. Device according to claim 11, characterized in that the resilient means is a coil spring (113) made by molding, at one end, with the mentioned tube (114), and at its other opposite end, with a sleeve (115) in which is received the connecting ferrule (11) of the needle.

16. Device according to claim 15, characterized in that the blocking means (120) is connected to the tube (114) and adapted to engage resiliently against the distal end of the tube to close the passage of the point toward its working position, during sliding of the tube toward its blocked protected position.

17. Device according to claim 11, characterized in that said tube (14, 114) having at its distal end (14a) a lower flat annular anti-sliding surface, constituted for example by roughening and/or clad with an adhesive material, said annular surface (14a) also serving to aim and target the vessel or the body space for the needle.

18. Device according to claim 11, characterized in that the tube (14, 114) has a longitudinal marking, for example a projecting rib or a colored line, arranged laterally so as not to mask the visibility of the needle and the periphery of the vessel or the body space to be reached, so as to enclose the general direction of the edges of the vessel or the body space.

* * * * *